(12) United States Patent
Ke et al.

(10) Patent No.: US 9,365,644 B2
(45) Date of Patent: Jun. 14, 2016

(54) ANTI-TNFα ANTIBODY

(75) Inventors: Yaohuang Ke, San Francisco, CA (US);
Guo-Liang Yu, Berkeley, CA (US)

(73) Assignee: EPITOMICS, INC., Burlingame, CA (US)

( * ) Notice: Subject to any disclaimer, the term of this patent is extended or adjusted under 35 U.S.C. 154(b) by 2115 days.

(21) Appl. No.: 12/425,763

(22) Filed: Apr. 17, 2009

(65) Prior Publication Data

US 2009/0269357 A1    Oct. 29, 2009

Related U.S. Application Data

(60) Provisional application No. 61/047,358, filed on Apr. 23, 2008.

(51) Int. Cl.
*A61K 39/395* (2006.01)
*C07K 16/24* (2006.01)

(52) U.S. Cl.
CPC ........... *C07K 16/241* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,530,101 | A | 6/1996 | Queen et al. |
| 5,859,205 | A * | 1/1999 | Adair et al. ................. 530/387.3 |
| 7,431,927 | B2 | 10/2008 | Couto et al. |
| 2003/0147891 | A1 | 8/2003 | Le et al. |
| 2003/0187231 | A1 | 10/2003 | Le et al. |
| 2003/0199679 | A1 | 10/2003 | Adair et al. |
| 2004/0002589 | A1 | 1/2004 | Rathjen et al. |
| 2004/0086979 | A1 | 5/2004 | Zhang et al. |
| 2004/0138427 | A1 | 7/2004 | Le et al. |
| 2004/0151722 | A1 | 8/2004 | Banerjee et al. |
| 2004/0185047 | A1 | 9/2004 | Giles-Komar et al. |
| 2005/0037008 | A1 | 2/2005 | Le et al. |
| 2006/0216293 | A1 | 9/2006 | Couto et al. |

FOREIGN PATENT DOCUMENTS

WO         2006050491 A2      5/2006

OTHER PUBLICATIONS

Eduardo Padlan, Mol Immunol. Feb. 1994;31(3):169-217.*
Vajdos et al., J Mol Biol. Jul. 5, 2002;320(2):415-28.*
Rudikoff et al., Proc. Natl. Acad. Sci. USA, 79: 1979-1 983, Mar. 1982.*
Colman P. M., Research in Immunology, 145:33-36, 1994.*
Short et al., vol. 277, No. 19, Issue of May 10, pp. 16365-16370, 2002.*
Balazovich, K., et al. Tumor necrosis factor-α and FMLP receptors are functionally linked during FMLP-stimulated activation of adherent human neutrophils. Blood. 1996, vol. 88, pp. 690-696.
Haranaka, K., et al. Purification and partial amino acid sequence of rabbit tumor necrosis factor. International Journal of Cancer. 1985, vol. 36, pp. 395-400.
Janeway, et al. Immunobiology: The Immune System in Health and Disease, Third Edition, New York: Garland Pub, 1997, pp. 2:19-21.
Nakatani, T., et al. Humanization of mouse anti-human IL-2 receptor anitbody B-B10. Protein Engineering. 1994, vol. 7, No. 3, pp. 435-443.
Piguet, P., et al. Evolution of collagen arthritis in mice is arrested by treatment with anti-tumour necrosis factor (TNF) antibody or a recombinant soluble TNF receptor. Immunology. 1992, vol. 77, pp. 510-514.
Reichmann, L., et al. Reshaping human antibodies for therapy. Nature. 1988, vol. 332, No. 24, pp. 323-327.
Spieker-Polet, H., et al. Rabbit monoclonal antibodies: Generating a fusion partner to produce rabbit-rabbit hybridomas. PNAS. 1995, vol. 92, pp. 9348-9352.
Williams, R., et al. Successful therapy of collagen-induced arthritis with TNF receptor-IgG fusion protein and combination with anti-CD4. Immunology. 1995, vol. 84, pp. 433-439.
EP App. No. 09735429.4, Extended European Search Report, dated May 18, 2012, 5pgs.
Burks, et al., "In vitro scanning saturation mutagenesis of an antibody binding pocket", Proc Natl Acad Sci, 1997, 94:412-17.
Chen, et al., "In vitro scanning saturation mutagenesis of all the specificity determining residues in an antibody binding site", Protein Engineering, 1999, 12:349-56.
Yu, et al., "A humanized anti-VEGF rabbit monoclonal antibody inhibits angiogenesis and blocks tumor growth in xenograft models", PLoS One, 2010, 5:e9072.

* cited by examiner

*Primary Examiner* — Zachary Skelding
(74) *Attorney, Agent, or Firm* — James S. Keddie; Bozicevic, Field & Francis, LLP

(57) ABSTRACT

An antibody that binds TNF α and neutralizes its activity is provided. In certain cases, the antibody comprises: a) a heavy chain variable domain comprising an amino acid sequence that is at least 95% identical to the amino acid sequence of SEQ ID NO. 1, and b) a light chain variable domain comprising an amino acid sequence that is at least 95% identical to the amino acid sequence of SEQ ID No. 2.

12 Claims, 6 Drawing Sheets

Fig. 1

```
VH: <-------FR1-------------->CDR1------FR2-----
    QQLQESGPGLVKPSETLSLTCAVSGFSLSRYGINWVRQAPGSGLEW
    SVK   EG  F  TD  T   T         VS    N    Q
                A                   T
    -->           CDR2          <-------FR3-------
    IGAIGETGRAYYASWAKSRSTISRDTSKNQVSLKMSSVTAADTAVY
    T    A   S FN R    V  NL T T R T L    Y
                                T V   T
                                E
    --->      CDR3       <---FR4--->
    FCARGELFNNGWGAFNIWGPGTMVTVSS
           V
           E                L

VK: <-------FR1-------------->  CDR1  <----FR2-----
    AYQMTQSPSSLSASVGDRVTIKCQASESIYSSLAWYQQKPGKPPKL
       D   T A V EP  GT      N  TG       Q
    --> CDR2  <-------------FR3-------------->
    LIYSASTLASGVPSRFSGSGSG-DFTLTISSLQPEDFATYCQQGF
       Q     S      K    EE   A  DVECA A S
                                       G A

CDR3    <---FR4--->
    GTSNVENPFGGGTKVEIK
    A  N         SE VV
```

HZ3-M, H chain
METGLRWLLLVAVLKGVQCQQLQESGPGLVKPSETLSLTCAVSGFSLSRYGINWVRQAPG
SGLEWIGAIGETGRAYYASWAKSRSTISRDTSKNQVSLKMSSVTAADTAVYFCARGELFN
NGWGAFNIWGPGTMVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK HZ3-M, Kappa L chain
MDTRAPTQLLGLLLLWLPGARCAYQMTQSPSSLSASVGDRVTIKCQASESIYSSLAWYQQ
KPGKPPKLLIYSASTLASGVPSRFSGSGSGTDFTLTISSLQPEDFATYYCQQGFGTSNVE
NPFGGGTKVEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC

Fig. 4

HZ3-M-Nterm, H chain
Leader sequence
MKHLWFFLLLVAAPRWVLSQVQLQESGPGLVKPSETLSLTCAVSGFSLSRYGINWVRQAPG
SGLEWIGAIGETGRAYYASWAKSRSTISRDTSKNQVSLKMSSVTAADTAVYFCARGELFN
NGWGAFNIWGPGTMVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDKKVEPK
SCDKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK HZ3-M-Nterm, Kappa L chain
MDMRVPAQLLGLLLLWLRGARCDIQMTQSPSSLSASVGDRVTIKCQASESIYSSLAWYQQ
KPGKPPKLLIYSASTLASGVPSRFSGSGSGTDFTLTISSLQPEDFATYYCQQGFGTSNVE
NPFGGGTKVEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC

Fig. 5

SEQUENCE LISTING

```
<160> NUMBER OF SEQ ID NOS: 12

<210> SEQ ID NO 1
<211> LENGTH: 120
<212> TYPE: PRT
<213> ORGANISM: Artificial Sequence
<220> FEATURE:
<223> OTHER INFORMATION: modified variable domain

<400> SEQUENCE: 1

Gln Gln Leu Gln Glu Ser Gly Pro Gly Leu Val Lys Pro Ser Glu Thr
1               5                   10                  15

Leu Ser Leu Thr Cys Ala Val Ser Gly Phe Ser Leu Ser Arg Tyr Gly
                20                  25                  30

Ile Asn Trp Val Arg Gln Ala Pro Gly Ser Gly Leu Glu Trp Ile Gly
            35                  40                  45

Ala Ile Gly Glu Thr Gly Arg Ala Tyr Tyr Ala Ser Trp Ala Lys Ser
        50                  55                  60

Arg Ser Thr Ile Ser Arg Asp Thr Ser Lys Asn Gln Val Ser Leu Lys
65                  70                  75                  80

Met Ser Ser Val Thr Ala Ala Asp Thr Ala Val Tyr Phe Cys Ala Arg
                85                  90                  95

Gly Glu Leu Phe Asn Asn Gly Trp Gly Ala Phe Asn Ile Trp Gly Pro
                100                 105                 110

Gly Thr Met Val Thr Val Ser Ser
            115                 120

<210> SEQ ID NO 2
<211> LENGTH: 110
<212> TYPE: PRT
<213> ORGANISM: Artificial Sequence
<220> FEATURE:
<223> OTHER INFORMATION: modified variable domain

<400> SEQUENCE: 2

Ala Tyr Gln Met Thr Gln Ser Pro Ser Ser Leu Ser Ala Ser Val Gly
1               5                   10                  15

Asp Arg Val Thr Ile Lys Cys Gln Ala Ser Glu Ser Ile Tyr Ser Ser
                20                  25                  30

Leu Ala Trp Tyr Gln Gln Lys Pro Gly Lys Pro Pro Lys Leu Leu Ile
            35                  40                  45

Tyr Ser Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Phe Gly Thr Ser Asn
                85                  90                  95

Val Glu Asn Pro Phe Gly Gly Gly Thr Lys Val Glu Ile Lys
                100                 105                 110
```

```
<210> SEQ ID NO 3
<211> LENGTH: 5
<212> TYPE: PRT
<213> ORGANISM: Artificial Sequence
<220> FEATURE:
<223> OTHER INFORMATION: modified variable domain fragment

<400> SEQUENCE: 3

Arg Tyr Gly Ile Asn
 1               5

<210> SEQ ID NO 4
<211> LENGTH: 16
<212> TYPE: PRT
<213> ORGANISM: Artificial Sequence
<220> FEATURE:
<223> OTHER INFORMATION: modified variable domain fragment

<400> SEQUENCE: 4

Ala Ile Gly Glu Thr Gly Arg Ala Tyr Tyr Ala Ser Trp Ala Lys Ser
 1               5                  10                  15

<210> SEQ ID NO 5
<211> LENGTH: 13
<212> TYPE: PRT
<213> ORGANISM: Artificial Sequence
<220> FEATURE:
<223> OTHER INFORMATION: modified variable domain fragment

<400> SEQUENCE: 5

Gly Glu Leu Phe Asn Asn Gly Trp Gly Ala Phe Asn Ile
 1               5                  10

<210> SEQ ID NO 6
<211> LENGTH: 11
<212> TYPE: PRT
<213> ORGANISM: Artificial Sequence
<220> FEATURE:
<223> OTHER INFORMATION: modified variable domain fragment

<400> SEQUENCE: 6

Gln Ala Ser Glu Ser Ile Tyr Ser Ser Leu Ala
 1               5                  10

<210> SEQ ID NO 7
<211> LENGTH: 7
<212> TYPE: PRT
<213> ORGANISM: Artificial Sequence
<220> FEATURE:
<223> OTHER INFORMATION: modified variable domain fragment

<400> SEQUENCE: 7

Ser Ala Ser Thr Leu Ala Ser
 1               5

<210> SEQ ID NO 8
<211> LENGTH: 12
<212> TYPE: PRT
<213> ORGANISM: Artificial Sequence
<220> FEATURE:
<223> OTHER INFORMATION: modified variable domain fragment

<400> SEQUENCE: 8

Gln Gln Gly Phe Gly Thr Ser Asn Val Glu Asn Pro
 1               5                  10
```

```
<210> SEQ ID NO 9
<211> LENGTH: 469
<212> TYPE: PRT
<213> ORGANISM: Artificial Sequence
<220> FEATURE:
<223> OTHER INFORMATION: modified variable domain

<400> SEQUENCE: 9

Met Glu Thr Gly Leu Arg Trp Leu Leu Leu Val Ala Val Leu Lys Gly
 1               5                  10                  15

Val Gln Cys Gln Gln Leu Gln Glu Ser Gly Pro Gly Leu Val Lys Pro
                20                  25                  30

Ser Glu Thr Leu Ser Leu Thr Cys Ala Val Ser Gly Phe Ser Leu Ser
            35                  40                  45

Arg Tyr Gly Ile Asn Trp Val Arg Gln Ala Pro Gly Ser Gly Leu Glu
        50                  55                  60

Trp Ile Gly Ala Ile Gly Glu Thr Gly Arg Ala Tyr Tyr Ala Ser Trp
 65                  70                  75                  80

Ala Lys Ser Arg Ser Thr Ile Ser Arg Asp Thr Ser Lys Asn Gln Val
                85                  90                  95

Ser Leu Lys Met Ser Ser Val Thr Ala Ala Asp Thr Ala Val Tyr Phe
            100                 105                 110

Cys Ala Arg Gly Glu Leu Phe Asn Asn Gly Trp Gly Ala Phe Asn Ile
        115                 120                 125

Trp Gly Pro Gly Thr Met Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
```

```
                    370                 375                 380
Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                    405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
450                 455                 460

Leu Ser Pro Gly Lys
465

<210> SEQ ID NO 10
<211> LENGTH: 239
<212> TYPE: PRT
<213> ORGANISM: Artificial Sequence
<220> FEATURE:
<223> OTHER INFORMATION: modified variable domain

<400> SEQUENCE: 10

Met Asp Thr Arg Ala Pro Thr Gln Leu Leu Gly Leu Leu Leu Leu Trp
1               5                   10                  15

Leu Pro Gly Ala Arg Cys Ala Tyr Gln Met Thr Gln Ser Pro Ser Ser
                20                  25                  30

Leu Ser Ala Ser Val Gly Asp Arg Val Thr Ile Lys Cys Gln Ala Ser
            35                  40                  45

Glu Ser Ile Tyr Ser Ser Leu Ala Trp Tyr Gln Gln Lys Pro Gly Lys
50                  55                  60

Pro Pro Lys Leu Leu Ile Tyr Ser Ala Ser Thr Leu Ala Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Gly Phe Gly Thr Ser Asn Val Glu Asn Pro Phe Gly Gly Gly Thr Lys
        115                 120                 125

Val Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 11
<211> LENGTH: 470
<212> TYPE: PRT
```

<213> ORGANISM: Artificial Sequence
<220> FEATURE:
<223> OTHER INFORMATION: modified variable domain

<400> SEQUENCE: 11

```
Met Lys His Leu Trp Phe Phe Leu Leu Leu Val Ala Ala Pro Arg Trp
  1               5                  10                  15

Val Leu Ser Gln Val Gln Leu Gln Glu Ser Gly Pro Gly Leu Val Lys
             20                  25                  30

Pro Ser Glu Thr Leu Ser Leu Thr Cys Ala Val Ser Gly Phe Ser Leu
         35                  40                  45

Ser Arg Tyr Gly Ile Asn Trp Val Arg Gln Ala Pro Gly Ser Gly Leu
     50                  55                  60

Glu Trp Ile Gly Ala Ile Gly Glu Thr Gly Arg Ala Tyr Tyr Ala Ser
 65                  70                  75                  80

Trp Ala Lys Ser Arg Ser Thr Ile Ser Arg Asp Thr Ser Lys Asn Gln
                 85                  90                  95

Val Ser Leu Lys Met Ser Ser Val Thr Ala Ala Asp Thr Ala Val Tyr
            100                 105                 110

Phe Cys Ala Arg Gly Glu Leu Phe Asn Asn Gly Trp Gly Ala Phe Asn
        115                 120                 125

Ile Trp Gly Pro Gly Thr Met Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
```

```
385                 390                 395                 400
Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
            450                 455                 460

Ser Leu Ser Pro Gly Lys
465             470

<210> SEQ ID NO 12
<211> LENGTH: 239
<212> TYPE: PRT
<213> ORGANISM: Artificial Sequence
<220> FEATURE:
<223> OTHER INFORMATION: modified variable domain

<400> SEQUENCE: 12

Met Asp Met Arg Val Pro Ala Gln Leu Leu Gly Leu Leu Leu Leu Trp
 1               5                  10                  15

Leu Arg Gly Ala Arg Cys Asp Ile Gln Met Thr Gln Ser Pro Ser Ser
                20                  25                  30

Leu Ser Ala Ser Val Gly Asp Arg Val Thr Ile Lys Cys Gln Ala Ser
            35                  40                  45

Glu Ser Ile Tyr Ser Ser Leu Ala Trp Tyr Gln Gln Lys Pro Gly Lys
        50                  55                  60

Pro Pro Lys Leu Leu Ile Tyr Ser Ala Ser Thr Leu Ala Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
                100                 105                 110

Gly Phe Gly Thr Ser Asn Val Glu Asn Pro Phe Gly Gly Gly Thr Lys
            115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

ANTI-TNFα ANTIBODY

BACKGROUND

Human tumor necrosis factor-alpha (TNFα) is a homotrimer consisting of three 17 kDa protein subunits (Eck M. J. et al., JBC, 267: 2119-2122, 1992; Smith R. A. et al., JBC, 262: 6951-6954, 1987). TNFα is an inflammatory cytokine secreted from macrophages and monocytes, and functions as a signal transmitter in several cellular reactions such as necrosis and apoptosis (Beyaert R. et al., FEBS Lett., 340: 9-16, 1994). TNFα causes a pro-inflammatory action leading to tissue destruction, such as breakdown of the cartilage and bone (Saklatvala, Nature, 322: 547-549, 1986), induction of procoagulation activity in vascular endothelial cells (Pober J S et al., J. Immunol., 136; 1680-1687, 1986), and increase in the adherence of neutrophils and lymphocytes (Pober et al., J. Immunol. 138: 3319-3324, 1987).

The pathology of a variety of disorders is attributed to excessive amounts of TNFα, either locally or systemically. For example, there is strong evidence that abnormally high production and release from cells of TNFα contributes to disease initiation and progression in rheumatoid arthritis, systemic inflammatory syndromes, diabetes, and multiple sclerosis. In every one of these conditions, the initiating and sustaining pathophysiologic action is directly a result of an immediate local release and synthesis of massive amounts of TNFα from several types of cells at or adjacent to the site of tissue damage. The locally released TNFα is followed by additional synthesis and release of TNFα by invading macrophages drawn to the site of tissue damage by a cascade of chemotactic cytokines released locally from cells in response to the greatly elevated TNFα concentrations.

There is a constant demand in the art for new antibodies that bind and neutralize TNFα.

SUMMARY

A TNFα neutralizing antibody is provided. In certain embodiments, an antibody may comprise a heavy chain variable domain comprising an amino acid sequence that is at least 95% identical to the amino acid sequence of SEQ ID NO: 1, and a light chain variable domain comprising an amino acid sequence that is at least 95% identical to the amino acid sequence of SEQ ID NO: 2. The antibody may be, for example, monoclonal, monovalent, bivalent, or single chain antibody. Methods of using a subject antibody to inhibit TNFα activity, methods of treatment using a subject antibody and kits containing the same are also provided. The subject antibody finds use in a variety of research and medical applications.

BRIEF DESCRIPTION OF THE DRAWINGS

FIG. 1 shows the amino acid sequence of the heavy (VH, SEQ ID NO. 1) and the light (VK, SEQ ID NO. 2) chain of a subject antibody. FR regions are labeled and CDRs are boxed and labeled. Underneath these sequences are potential amino acid substitutions that would be expected to result in an active antibody.

FIG. 4 shows the amino acid sequence of HZD-M RabMAb (SEQ ID NOS: 9 and 10). The leader sequences of the heavy and light chains are underlined, the variable domains are shown in bold, and the constant regions are underlined and bolded. The variable domains of the HZD RabMAb contain the amino acid sequences of SEQ ID NO:1 and 2.

FIG. 5 shows the amino acid sequence of HZD-N-Nterm RabMAb (SEQ ID NOS: 11 and 12). The leader sequences of the heavy and light chains are underlined, the variable domains are shown in bold, and the constant regions are underlined and bolded. The variable domains of the HZD RabMAb are identical the amino acid sequences of SEQ ID NO:1 and 2, except for amino acid changes at the N-terminus.

DEFINITIONS

Figure 2A:
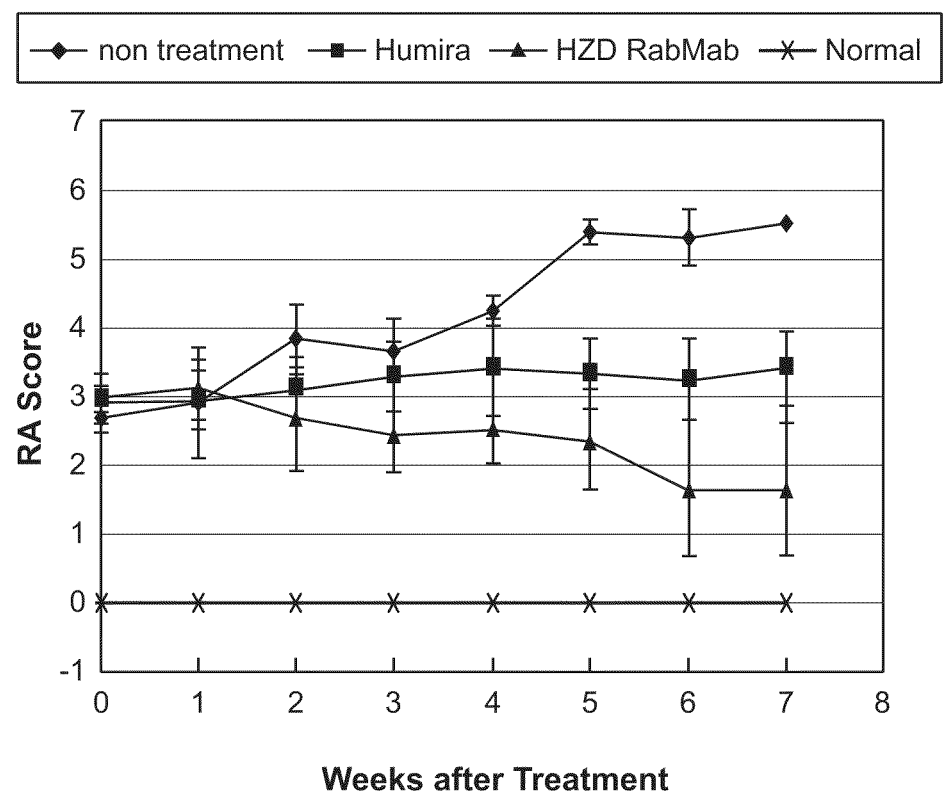
FIG. 2A is a graph showing the RA scores for mice subjected to different treatments.

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antibody" includes a plurality of such antibodies and reference to "a framework region" includes reference to one or more framework regions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to Fab, Fv, scFv, and Fd fragments, chimeric antibodies, humanized antibodies, single-chain antibodies, fusion proteins comprising an antigen-binding portion of an antibody and a non-antibody protein, and antibodies that have post-translational modifications. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies.

Antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986)).

An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The numbering of all antibody amino acid sequences discussed herein conforms to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

Chimeric antibodies are antibodies whose light and heavy chain genes have been constructed, typically by genetic engineering, from antibody variable and constant region genes belonging to different species. For example, the variable segments of the genes from a rabbit monoclonal antibody may be joined to human constant segments, such as gamma 1 and gamma 3. An example of a therapeutic chimeric antibody is a hybrid protein composed of the variable or antigen-binding domain from a rabbit antibody and the constant or effector domain from a human antibody (e.g., the anti-Tac chimeric antibody made by the cells of A.T.C.C. deposit Accession No. CRL 9688), although other mammalian species may be used.

As used herein, the term "humanized antibody" or "humanized immunoglobulin" refers to an non-human (e.g., mouse or rabbit) antibody containing one or more amino acids (in a framework region, a constant region or a CDR, for example) that have been substituted with a correspondingly positioned amino acid from a human antibody. In general, humanized antibodies may produce a reduced immune response in a human host, as compared to a non-humanized version of the same antibody.

It is understood that the humanized antibodies designed and produced by the present method may have additional conservative amino acid substitutions which have substantially no effect on antigen binding or other antibody functions. By conservative substitutions is intended combinations such as those from the following groups: gly, ala; val, ile, leu; asp, glu; asn, gln; ser, thr; lys, arg; and phe, tyr. Amino acids that are not present in the same group are "substantially different" amino acids.

The term "specific binding" refers to the ability of an antibody to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between a capture agent and analyte when they are specifically bound in a capture agent/analyte complex is characterized by a $K_D$ (dissociation constant) of less than $10^{-6}$ M, less than $10^{-7}$ M, less than $10^{-8}$ M, less than $10^{-9}$ M, less than $10^{-9}$ M, less than $10^{-11}$ M, or less than about $10^{-12}$ M or less.

A "variable region" of a heavy or light antibody chain is an N-terminal mature domain of the chains. All domains, CDRs and residue numbers are assigned on the basis of sequence alignments and structural knowledge. Identification and numbering of framework and CDR residues is as described in by Chothia and others (Chothia, Structural determinants in the sequences of immunoglobulin variable domain. J Mol Biol 1998; 278: 457-79).

VH is the variable domain of an antibody heavy chain. VL is the variable domain of an antibody light chain, which could be of the kappa (K) or of the lambda isotype. K-1 antibodies have the kappa-1 isotype whereas K-2 antibodies have the kappa-2 isotype and VL is the variable lambda light chain. The variable domain of an antibody contains a heavy chain variable domain and a light chain variable domain.

As used herein, the terms "determining," "measuring," and "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Polypeptides may be of any size, and the term "peptide" refers to polypeptides that are 8-50 residues (e.g., 8-20 residues) in length.

As used herein the term "isolated," when used in the context of an isolated antibody, refers to an antibody of interest that is at least 60% free, at least 75% free, at least 90% free, at least 95% free, at least 98% free, and even at least 99% free from other components with which the antibody is associated with prior to purification.

The terms "treatment", "treating" and the like are used herein to refer to any treatment of any disease or condition in a mammal, e.g., particularly a human or a mouse, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., arresting its development and/or delaying its onset or manifestation in the patient; and/or c) relieving a disease, condition, or symptom of a disease or condition, e.g., causing regression of the condition or disease and/or its symptoms.

The terms "subject", "host", "patient" and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

"Corresponding amino acids" are amino acid residues that are at an identical position (i.e., they lie across from each other) when two or more amino acid sequences are aligned. Methods for aligning and numbering antibody sequences are set forth in great detail in Chothia, supra, Kabat supra, and others. As is known in the art (see, e.g., Kabat 1991 Sequences of Proteins of Immunological Interest, DHHS, Washington, D.C.), sometimes one, two or three gaps and/or insertions of up to one, two, three or four residues, or up to about 15 residues (particularly in the L3 and H3 CDRs) may be made to one or both of the amino acids of an antibody in order to accomplish an alignment.

A "natural" antibody is an antibody in which the heavy and light immunoglobulins of the antibody have been naturally selected by the immune system of a multi-cellular organism, as opposed to unnaturally paired antibodies made by e.g., phage display, or humanized antibodies. As such, the subject parental antibodies do not usually contain any viral (e.g., bacteriophage M13)-derived sequences. Spleen, lymph nodes and bone marrow are examples of tissues that produce natural antibodies.

A "substitutable position" is a particular position of an antibody that may be substituted by different amino acids without significantly decreasing the binding activity of the antibody. Methods for identifying substitutable positions, and how they may be substituted, are described in much greater detail below. A substitutable positions may also be referred to as "variation tolerant position".

A "parent" antibody is an antibody that is the target of amino acid substitutions. In certain embodiments, amino acids may be "donated" by a "donor" antibody to the parent antibody to produce an altered antibody.

"Related antibodies" are antibodies that have a similar sequence and produced by cells that have a common B cell ancestor. Such a B cell ancestor contains a genome having a rearranged light chain VJC region and a rearranged heavy chain VDJC region, and produces an antibody that has not yet undergone affinity maturation. "Naïve" or "virgin" B cells present in spleen tissue are exemplary B cell common ancestors. Related antibodies bind to the same epitope of an antigen and are typically very similar in sequence, particularly in their L3 and H3 CDRs. Both the H3 and L3 CDRs of related antibodies have an identical length and a near identical sequence (i.e., differ by 0, 1 or 2 residues). Related antibodies are related via a common antibody ancestor, the antibody produced in the naïve B cell ancestor. The term "related antibodies" is not intended to describe a group of antibodies that do not have a common antibody ancestor produced by a B-cell.

The term "TNFα" or its non-abbreviated form "tumor necrosis factor-α", as used herein, is intended to refer to a human cytokine that exists as a 17 kD secreted form and a 26 kD membrane associated form, the biologically active form of which is composed of a trimer of noncovalently bound 17 kD molecules. The structure of TNFα is described further in, for example, Pennica et al. (Nature 1984 312:724-729), Davis et al. (Biochemistry 1987 26:1322-1326) and Jones et al. (Nature 1989 338:225-228). The term TNFα is intended to include recombinant TNFα molecules, which can be prepared by standard recombinant expression methods or purchased commercially (R & D Systems, Catalog No. 210-TA, Minneapolis, Minn.), as well as fusion proteins containing a TNFα molecule. Amino acid sequences of exemplary TNFαs that may be employed herein are found in the NCBI's Genbank database and a full description of human TNFα and its role in various diseases and conditions is found in NCBI's Online Mendelian Inheritance in Man database.

A "TNFα neutralizing antibody", "antibody that neutralizes TNFα activity" or any grammatical equivalent thereof, is intended to refer to an antibody whose binding to TNFα results in inhibition of a biological activity of TNFα. This inhibition of the biological activity of TNFα can be assessed by measuring one or more indicators of TNFα biological activity, such as TNFα-induced cytotoxicity (either in vitro or in vivo), TNFα-induced cellular activation or TNFα binding to a TNFα receptor. TNFα biological activity can be assessed by one or more of several standard in vitro or in vivo assays known in the art.

DETAILED DESCRIPTION OF PREFERRED EMBODIMENTS

A TNFα neutralizing antibody is provided. In certain embodiments, an antibody may comprise a heavy chain variable domain comprising an amino acid sequence that is at least 95% identical to the amino acid sequence of SEQ ID NO. 1, and a light chain variable domain comprising an amino acid sequence that is at least 95% identical to the amino acid sequence of SEQ ID No. 2. The antibody may be, for example, monoclonal, monovalent, bivalent, or single chain antibody. Methods of using a subject antibody to inhibit TNFα activity, methods of treatment using a subject antibody and kits containing the same are also provided. The subject antibody finds use in a variety of research and medical applications.

In certain embodiments, a monoclonal antibody may comprise a variable domain comprising: a heavy chain variable domain comprising the CDR1 (RYGIN; SEQ ID NO: 3), CDR2 (AIGETGRAYYASWAKS; SEQ ID NO: 4), and CDR3 (GELFNNGWGAFNI; SEQ ID NO: 5)) regions of SEQ ID NO: 1; and a light chain variable domain comprising the CDR1 (QASESIYSSLA; SEQ ID NO: 6), CDR2 (SASTLAS; SEQ ID NO: 7), and CDR3 (QQGFGTSNVENP; SEQ ID NO: 8) regions of SEQ ID NO: 2; or a variant of the variable domain that is otherwise identical to the variable domain except for up to 6 amino acid substitutions (i.e., 1, 2, 3, 4, 5 or 5 substitutions) in the CDR regions (i.e., the 6 CDR regions, collectively, may contain up to a total of 6 amino acid substitutions), where the monoclonal antibody neutralizes TNFα activity.

In other embodiments, the antibody may comprise a) a heavy chain variable domain that differs in amino acid sequence from SEQ ID NO: 1 by up to about 6 amino acid substitutions, e.g., 1, 2, 3, 4, 5 or 6 substitutions, and b) a light chain variable domain that differs in amino acid sequence from SEQ ID NO: 2 by up to about 6 amino acid substitutions, e.g., 1, 2, 3, 4, 5 or 6 substitutions. Exemplary amino acid substitutions are shown below. A subject antibody may have any one or combination of these substitutions.

TABLE 1

Exemplary amino acid substitutions in the heavy chain variable domain.

| Amino acid position | SEQ ID No. 1 | Substitution |
|---|---|---|
| 2 (FR1) | Q | S |
| 3 (FR1) | L | V |
| 4 (FR1) | Q | K |
| 7 (FR1) | G | E |
| 8 (FR1) | P | G |
| 11 (FR1) | V | F |
| 14 (FR1) | S | T/A |
| 15 (FR1) | E | D |
| 18 (FR1) | S | T |
| 22 (FR1) | A | T |
| 33 (CDR1) | I | V |
| 34 (CDR1) | N | S/T |
| 42 (FR2) | S | N |
| 45 (FR2) | E | Q |
| 49 (CDR2) | A | T |
| 53 (CDR2) | T | A |
| 56 (CDR2) | A | S |
| 58 (CDR2) | Y | F |
| 60 (CDR2) | S | N |
| 63 (CDR2) | K | R |
| 68 (FR3) | I | V |
| 69 (FR3) | S | T |
| 71 (FR3) | D | N/T |
| 73 (FR3) | S | N |
| 74 (FR3) | K | L/V/E |
| 76 (FR3) | Q | T |
| 78 (FR3) | S | T |
| 80 (FR3) | K | R/T |
| 82 (FR3) | S | T |
| 84 (FR3) | V | L |
| 91 (FR3) | V | T |
| 99 (CDR3) | L | V/E |
| 115 (FR4) | M | L |

TABLE 2

Exemplary amino acid substitutions in the light chain variable domain.

| Amino acid position | SEQ ID No. 2 | Substitution |
|---|---|---|
| 3 (FR1) | Q | D |
| 7 (FR1) | S | T |
| 9 (FR1) | S | A |
| 11 (FR1) | L | V |
| 13 (FR1) | A | E |
| 14 (FR1) | S | P |
| 17 (FR1) | D | G |
| 18 (FR1) | R | T |
| 28 (CDR1) | S | N |
| 31 (CDR1) | S | T |
| 32 (CDR1) | S | G |
| 42 (FR2) | K | Q |
| 50 (CDR2) | S | Q |
| 59 (FR3) | P | S |
| 63 (FR3) | S | K |
| 70 (FR3) | D | E |
| 71 (FR3) | F | E |
| 74 (FR3) | T | A |
| 77 (FR3) | S | D/G |
| 78 (FR3) | L | V |
| 79 (FR3) | Q | E/A |
| 80 (FR3) | P | C |
| 81 (FR3) | E | A |
| 83 (FR3) | F | A |
| 85 (FR3) | T | S |
| 93 (CDR3) | G | A |
| 95 (CDR3) | S | N |
| 105 (FR4) | T | S |
| 106 (FR4) | K | E |
| 108 (FR4) | E | V |
| 109 (FR4) | I | V |

These exemplary amino acid substitutions are also shown in FIG. 1. An antibody having any of these substitutions should neutralize TNFα activity as antibodies with all of these substitutions have been shown to neutralize TNFα activity. TNFα-neutralizing antibodies containing amino acids at these positions are disclosed in US patent application publication no. 20060216293, which is herein incorporated by reference. In certain embodiments, subject antibody may be a humanized version of the antibodies disclosed in US patent application no. 20060216293.

The amino acid substitutions may be in both the frame work regions and the CDRs, or solely in the frame work regions or the CDRs. Thus, in certain embodiments the frame work regions of the heavy chain variable domain may collectively differ in amino acid sequence from SEQ ID NO. 1 by up to about 6 amino acid substitutions, e.g., 1, 2, 3, 4, 5 or 6 substitutions, and the frame work regions of the light chain variable domain may collectively differ in amino acid sequence from SEQ ID NO. 2 by up to about 6 amino acid substitutions, e.g., 1, 2, 3, 4, 5 or 6 substitutions.

In some antibodies, the amino acid substitutions may all be in the CDRs. Thus the CDRs of the heavy chain variable domain may collectively differ in amino acid sequence from SEQ ID NO. 1 by up to about 6 amino acid substitutions, e.g., 1, 2, 3, 4, 5 or 6 substitutions, and the CDRs of the light chain variable domain may collectively differ in amino acid sequence from SEQ ID NO. 2 by up to about 6 amino acid substitutions, e.g., 1, 2, 3, 4, 5 or 6 substitutions.

In particular embodiments, the antibody may comprise a) a heavy chain variable domain comprising an amino acid sequence that is identical to the amino acid sequence of SEQ ID NO. 1 and b) a light chain variable domain comprising an amino acid sequence that is identical to the amino acid sequence of SEQ ID NO. 2.

In particular embodiments, the antibody may comprise a) a heavy chain variable domain that is at least about 95% identical in amino acid sequence to SEQ ID NO. 1 and b) a light chain variable domain that is at least about 95% identical in amino acid sequence to SEQ ID NO. 2. Thus, the subject antibody might have a) a heavy chain variable domain that is at least about 95%, 96%, 97%, 98%, 99% or 100% identical in amino acid sequence to SEQ ID NO. 1 and b) a light chain variable domain that is at least about 95%, 96%, 97%, 98%, 99% or 100% identical in amino acid sequence to SEQ ID NO. 2.

In addition to the amino acid substitutions described above, a subject antibody may have additional amino acids at either end of the heavy and light chains. For example, a subject antibody may contain at least 1, 2, 3, 4, 5, or 6 or more at the C or N-terminal end of the heavy and/or light chains, independently. In certain cases, a subject antibody may be shorter than the exemplary antibody described herein, by 1, 2, 3, 4, 5, or 6 amino acids at either end of the heavy and light chains, independently.

The subject antibody may be humanized. In general, humanized antibodies are made by substituting amino acids in the framework regions of a parent antibody to produce a modified antibody that may be less immunogenic in a human than the parent antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585, 089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323, 1988). Antibodies can be humanized in accordance to methods described set forth in great detail in U.S. patent application Ser. No. 10/984,473, filed on Nov. 8, 2004 and entitled "Methods for antibody engineering", which application is incorporated by reference in its entirety. In general, this humanization method involves identifying a substitutable position of an antibody by comparing sequences of antibodies that bind to the same antigen, and replacing the amino acid at that position with a different amino acid that is present at the same position of a similar human antibody. In these methods, the amino acid sequence of a parental antibody is compared to (i.e., aligned with) the amino acid sequences of other related antibodies to identify variation tolerant positions. The amino acid sequence of the variable domain of the parental antibody is usually compared to a database of human antibody sequences, and a human antibody that has an amino acid sequence that is similar to that of the parental antibody is selected. The amino acid sequences of the parental antibody and the human antibody are compared (e.g., aligned), and amino acids at one or more of the variation tolerant positions of the parental antibody are substituted by correspondingly positioned amino acids in the human antibody.

The above-discussed variation tolerant position substitution methods are readily incorporated into any known humanization method and are also readily employed to produce humanized antibodies containing CDR regions that are altered with respect to the CDR regions of the parent antibody. Accordingly humanized TNFα neutralizing antibodies containing altered versions of the CDRs of the parent antibodies are provided.

Antibodies that Neutralize TNFα Activity

In certain embodiments, a subject antibody may be employed to bind TNFα and neutralize its activity. A TNFα neutralizing antibody inhibits at least one activity of TNFα in the range of about 20% to 100%, e.g., by at least about 10%, at least about 20%, at least about 30%, at least about 40%, at least about 50%, at least about 60%, usually up to about 70%, up to about 80%, up to about 90% or more. In any of these assays, a subject antibody inhibits TNFα activity with an $IC_{50}$ of $1\times10^{-7}$ M or less (e.g., $1\times10^{-7}$ M or less, $1\times10^{-8}$ M or less, $1\times10^{-9}$ M or less, usually to $1\times10^{-12}$ M or $1\times10^{-13}$ M). In assays in which a mouse is employed, a subject antibody typically has an $ED_{50}$ of less then 1 μg/mouse (e.g., 10 ng/mouse to 1 μg/mouse).

TNFα activity can be assayed in a variety of ways, including, but not limited to: assays for TNFα-induced cytotoxicity (either in vitro or in vivo) using suitable cells, e.g., L929 cells; assays for binding of TNFα to its receptor using suitable cells, e.g., U-937 cells; assays for inhibition of endothelial cell leukocyte adhesion molecule 1 (ELAM-1) expression on human umbilical vein endothelian (HEVEC) cells; or in vivo assays using D-galactosamine sensitized mice. Such assays are described in great detail in U.S. Pat. No. 6,090,382, which is incorporated by reference herein for that purpose.

Certain embodiments of the subject antibody have the following general characteristics:
a) high affinity for TNFα (e.g., a $K_d$ of $10^{-8}$ or less);
b) slow off rate for dissociation with TNFα (e.g., a $K_{off}$ of $10^{-3}$ sec$^{-1}$ or less); and
c) TNFα neutralizing activity.

Methods for measuring binding affinity, off rate and other antibody binding kinetics are well known in the art, and may be employed to determine whether an antibody has a high affinity and a slow off rate for TNFα. In many methods and as is well known in the art, antibody binding kinetics may be measured by ELISA methods or by measuring surface plasmon resonance using, for example, a BIACORE™ biosensor sold by Pharmacia (now Pfizer). Methods for measuring binding of antigens to antibodies using surface plasmon resonance are well known in the art (see, e.g., Methods of Dev. Biol. 2003 112:141-51 and J. Mol. Recognit. 1999 12:310-5) and are readily adapted for use herein.

The antibody may be a full-length natural antibody or any chimera thereof, for example. Methods for producing chimeric antibodies are known in the art. See e.g., Morrison et al (Science 1985 229:1202); Oi et al (BioTechniques 1986 4:214); Gillies et al. (J. Immunol. Methods 1989 125:191-202) and U.S. Pat. Nos. 5,807,715, 4,816,567 and 4,816,397, which are incorporated herein by reference in their entirety. In certain embodiments, the subject antibody may be monoclonal, monovalent, bivalent, or single chain antibody.

Methods of Using Antibodies to Inhibit TNFα Activity

Subject antibody may be employed in a method of inhibiting TNFα activity. The subject antibody may be employed in a variety of protocols described below.

The protocols that may be employed in these methods are numerous, and include but are not limited to cell-free assays, e.g., binding assays to a TNFα receptor; cellular assays in which a cellular phenotype is measured, e.g., gene expression or cytotoxicity; and in vivo assays that involve a particular animal (which, in certain embodiments may be an animal model for a TNFα-related condition).

Such assays, including those described above, are well known in the art and are described in a variety of publications, including 20040151722, 20050037008, 20040185047, 20040138427, 20030187231, 20040002589, 20030199679, U.S. Pat. No. 6,090,382 and Balazovich (Blood 1996 88: 690-696).

Methods for Producing Antibodies

In many embodiments, the nucleic acids encoding a subject antibody are introduced directly into a host cell, and the cell incubated under conditions sufficient to induce expression of the encoded antibody.

Any cell suitable for expression of expression cassettes may be used as a host cell. For example, yeast, insect, plant, etc., cells. In many embodiments, a mammalian host cell line that does not ordinarily produce antibodies is used, examples of which are as follows: monkey kidney cells (COS cells), monkey kidney CVI cells transformed by SV40 (COS-7, ATCC CRL 165 1); human embryonic kidney cells (HEK-293, Graham et al. J. Gen Virol. 36:59 (1977)); baby hamster kidney cells (BHK, ATCC CCL 10); chinese hamster ovary-cells (CHO, Urlaub and Chasin, Proc. Natl. Acad. Sci. (USA) 77:4216, (1980); mouse sertoli cells (TM4, Mather, Biol. Reprod. 23:243-251 (1980)); monkey kidney cells (CVI ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (hep G2, HB 8065); mouse mammary tumor (MMT 060562, ATCC CCL 51); TRI cells (Mather et al., Annals N.Y. Acad. Sci. 383:44-68 (1982)); NIH/3T3 cells (ATCC CRL-1658); and mouse L cells (ATCC CCL-1). Additional cell lines will become apparent to those of ordinary skill in the art. A wide variety of cell lines are available from the American Type Culture Collection, 10801 University Boulevard, Manassas, Va. 20110-2209.

Methods of introducing nucleic acids into cells are well known in the art. Suitable methods include electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995. In some embodiments lipofectamine and calcium mediated gene transfer technologies are used.

After the subject nucleic acids have been introduced into a cell, the cell is typically incubated, normally at 37° C., sometimes under selection, for a period of about 1-24 hours in order to allow for the expression of the antibody. In most embodiments, the antibody is typically secreted into the supernatant of the media in which the cell is growing in.

In mammalian host cells, a number of viral-based expression systems may be utilized to express a subject antibody. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). The efficiency of expression may be enhanced by the inclusion of appropriate transcription enhancer elements, transcription terminators, etc. (see Bittner et al., Methods in Enzymol. 153:51-544 (1987)).

For long-term, high-yield production of recombinant antibodies, stable expression may be used. For example, cell lines, which stably express the antibody molecule may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds that interact directly or indirectly with the antibody molecule.

Once an antibody molecule of the invention has been produced, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

Antibody Conjugates

In certain embodiments, subject antibody may be conjugated to an agent. Any agent would be suitable so long as its conjugation to the antibody does not substantially reduce a desired function and/or characteristic of the antibody. For example, in some embodiments, an immunoconjugate comprises an agent which is a cytotoxic agent. In some embodiments, said cytotoxic agent is selected from the group consisting of a radioactive isotope, a chemotherapeutic agent and a toxin. In some embodiments, said toxin is selected from the group consisting of doxorubicin, methotrexate, maytansine, ricin, diphtheria toxin and trichothene. The use of antibody-drug conjugates for the local delivery of cytotoxic or cyto-static agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) theoretically allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies 84: Biological And Clinical Applications, A. Pinchera et al. (ed.s), pp. 475-506). For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in using a number of methods known in the art. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

In some embodiments, an immunoconjugate comprises an agent which is a detectable marker. In some embodiments, said detectable marker is selected from the group consisting of a radioactive isotope, a member of a ligand-receptor pair, a member of an enzyme-substrate pair and a member of a fluorescence resonance energy transfer pair.

Formulations and Administration

The antibodies of the invention may be administered in any manner which is medically acceptable. This may include injections, by parenteral routes such as intravenous, intravascular, intraarterial, subcutaneous, intramuscular, intratumor, intraperitoneal, intraventricular, intraepidural, or others as well as oral, nasal, ophthalmic, rectal, or topical. Sustained release administration is also specifically included in the invention, by such means as depot injections or erodible implants. Localized delivery is particularly contemplated, by such means as delivery via a catheter to one or more arteries, such as the renal artery or a vessel supplying a localized tumor.

The subject antibodies may be a pharmaceutically acceptable carrier. The term "pharmaceutically acceptable carrier" means one or more organic or inorganic ingredients, natural or synthetic, with which the antibody is combined to facilitate its application. A suitable carrier includes sterile saline although other aqueous and non-aqueous isotonic sterile solutions and sterile suspensions known to be pharmaceutically acceptable are known to those of ordinary skill in the art. An "effective amount" refers to that amount which is capable of ameliorating or delaying progression of the diseased, degenerative or damaged condition. An effective amount can be determined on an individual basis and will be based, in part, on consideration of the symptoms to be treated and results sought. An effective amount can be determined by one of ordinary skill in the art employing such factors and using no more than routine experimentation.

In one embodiment a subject antibody is administered to a patient by intravenous, intramuscular or subcutaneous injection. An antibody may be administered within a dose range between about 0.1 mg/kg to about 100 mg/kg; between about 1 mg/kg to 75 mg/kg; or about 10 mg/kg to 50 mg/kg. The antibody may be administered, for example, by bolus injunction or by slow infusion. Slow infusion over a period of 30 minutes to 2 hours may be used.

Utility

The subject antibodies are useful for treating a TNFα-mediated disorder. In one embodiment, the invention provides a method of treating a subject for a TNFα-related condition. The method generally involves administering a subject antibody a subject having a TNFα-related disorder in an amount effective to treat at least one symptom of the TNFα-related disorder.

The term "TNFα-mediated disorder" refers to any disorder or disease state in which TNF-α plays a direct role, e.g., by excessive production or release of TNFα itself or by TNFα-induced production or release of another agent that produces a pathological effect. As such, the subject methods are useful for treating any fibrotic disorder, including obliterative bronchiolitis, interstitial lung disease, fibrotic lung disease (e.g., idiopathic pulmonary fibrosis (IPF), pulmonary fibrosis of a known etiology, cystic fibrosis, adult respiratory distress, syndrome (ARDS), tumor stroma in lung disease, systemic sclerosis, Hermansky-Pudlak syndrome (HPS), coal worker's pneumoconiosis (CWP), asbestosis, sarcoidosis, silicosis, black lung disease, chronic pulmonary hypertension, AIDS associated pulmonary hypertension, and the like), human kidney disease (e.g., nephrotic syndrome, Alport's syndrome, HIV-associated nephropathy, polycystic kidney disease, Fabry's disease, diabetic nephropathy, and the like), glomerular nephritis, nephritis associated with systemic lupus erythematosus, fibrotic vascular disease, arterial sclerosis, atherosclerosis, varicose veins, coronary infarcts, cerebral infarcts, musculoskeletal fibrosis, post-surgical adhesions, cutis keloid formation, progressive systemic sclerosis, primary sclerosing cholangitis (PSC), renal fibrosis, scleroderma (local and systemic), diabetic retinopathy, glaucoma, Peyronie's disease, penis fibrosis, artherostenosis after test using cystoscope, inner accretion after surgery, myelofibrosis, idiopathic retroperitoneal fibrosis, fibrosis incident to microbial infection (e.g. viral, bacterial, fungal, parasitic, etc.), fibrosis incident to inflammatory bowel disease (including stricture formation in Crohn's disease and microscopic colitis), fibrosis induced by chemical or environmental insult (e.g., cancer chemotherapy, pesticides, radiation (e.g. cancer radiotherapy), and the like), peritoneal fibrosis, liver fibrosis, myocardial fibrosis, pulmonary fibrosis, Grave's ophthalmopathy, drug induced ergotism, cardiovascular disease, fibrosis incident to benign or malignant cancer (including desmoid tumor), Alzheimer's disease, scarring, scleroderma, glioblastoma in Li-Fraumeni syndrome, sporadic glioblastoma, myeloid leukemia, acute myelogenous leukemia, myelodysplastic syndrome, myeloproliferative syndrome, fibrosis incident to benign or malignant gynecological cancer (e.g., ovarian cancer, Lynch syndrome, and the like), Kaposi's sarcoma, Hansen's disease, inflammatory bowel disease (including stricture formation in Crohn's disease and microscopic colitis), Crohn's disease, ulcerative colitis, multiple sclerosis, Type II diabetes, rheumatoid arthritis, asthma, chronic bronchitis, atopic dermatitis, urticaria, allergic rhinitis, allergic conjunctivitis, chronic obstructive pulmonary disease, graft rejection, graft-versus-host disease, sepsis, and the like.

Some of these disorders are described in greater detail below.

CNS Disorders

Evidence exists in the literature that TNFα has effects on cells of the central nervous systems (CNS). Evidence for CNS production of TNFα, involvement of TNFα in brain injury, the role of polymorphonuclear leukocytes (PMNs) in brain injury, the role of adhesion molecules in brain injury, and potential TNFα directed therapeutic strategies for prevention of brain injury have been reviewed in the literature. See, e.g., Babak Arvin et al. (1995) Ann. N.Y. Acad. Sciences 765:62-71.

The prevention of brain edema by anti-TNFα antibodies in experimental meningitis provides firm evidence for the involvement of TNFα in the breakdown of the Blood Brain Barrier. TNFα can also trigger the infiltration of neutrophils into the tissue with consequent induction of secondary mediators in local areas. See, e.g., "Cytokines and CNS," Edit: R. M. Ransohoff and E. N. Beneviste, CRC Press, Page 193, 1996).

Closed head injury (CHI) in rats triggers the production of TNFα in the contused brain hemisphere, and it was shown that a decrease in TNFα levels or inhibition of its activity is accompanied by significantly reduced brain damage. Shohami et al. (1996) J. Cerebral Blood Flow Metab., 16:378-384.

Multiple Sclerosis

Multiple sclerosis (MS) plaques within the CNS are infiltrated by peripheral blood mononuclear cells. In patients, TNFα, but not lymphotoxin, is overproduced by peripheral blood mononuclear cells during MS relapse. Glabinski et al. (1995) Neurol Scand. 91:276-279. TNFα has an ability to cause cell death of oligodendrocytes in vitro. Robbins et al. (1987) J. Immunol., 139:2593. This aspect of TNFα activity may contribute directly to myelin damage and/or the demyelination process observed in diseases such as multiple sclerosis (MS). TNFα has been shown to play a central role in the demyelination of the CNS in MS. Serum levels of TNFα are elevated in patients with active MS, and TNFα producing macrophages, microglia and astrocytes are present at active lesion sites. In in vitro experiments, TNFα directly mediates oligodendrocyte damage and suppresses myelin formation, and it stimulates astrocytes, which are then responsible for the CNS scarring plaques in MS (Owens and Sriram, Neurological Clinics, 13:51, 1995).

Serum levels of TNFα are elevated in patients with active MS (M. Chofflon et al., Eur. Cytokine Net., 3:523, 1991; Sharief, M. K. and Hentgen, N. E. Jour. Med., 325:467, 1991). TNFα producing macrophages/microglia and astrocytes are present at active lesion sites (K. Selmaj al., Jour. Clin. Invest., 87:949, 1991). In in vitro experiments, TNFα directly mediates oligodendrocyte damage and suppresses myelin formation (K. Selmaj et al., J. Immunol., 147:1522, 1990); T. Tsumamoto et al., Acta Neurol. Scand., 91:71, 1995), and it stimulates astrocytes, which are responsible for the scarring plaques (K. Selmaj et al., J. Immunol., 144:129, 1990).

An increase in TNFα expression preceding MS exacerbation attacks has been shown. ("Cytokines and the CNS," Edit: R. M. Ransohoff and E. N. Beneviste, CRC Press, 1996, p. 232). In vivo studies of murine, rat and human demyelinating diseases indicate that TNFα participates in the inflammatory reactions that take place within the CNS. TNFα positive astrocytes and macrophages have been identified in the brains of MS patients, particularly in the plaque region (F. M. Hofman et al., J. Exp. Med., 170:607, 1991, and Selmaj et al., J. Clin. Invest., 87:949, 1991) have determined that both TNFα and TNF-β are present in MS plaque regions, and that TNFα is localized within astroyctes, whereas TNFα is associated with microglia and T-cells. Increased serum and cerebrospinal fluid levels of TNFα have been documented in patients with MS (Sharief, M. K., M. Phil, and R. Hentges, N. Engl. J. Med., 325:467, 1991), and a strong correlation exists between cerebrospinal fluid levels of TNFα, disruption of the blood brain barrier, and high levels of circulating ICAM-1 in patients with active MS.

Alzheimer's Disease

Alzheimer's disease (AD), the most common dementing disorder of late life, is a major cause of disability and death in the elderly. The disease is manifested by the appearance of abnormalities in the brain, particularly involving the hippocampus, amygdala, thalamus and neocortex. Lesions in these regions are associated with dysfunction/death of neurons and deafferentation of targets. The principal pathological hallmarks of AD are deposits of the amyloid-β protein (Aβ) in extracellular parenchyma and cerebral vessels, and neurofibrillary tangles.

TNFα has been generally elevated in the serum of AD patients based upon both antibody assays and bioassays. In one study almost half of the AD cases had elevated TNFα, but none of the controls had a similar elevation. The blood-brain barrier does not normally permit passage of cytokines. However, there is evidence to suggest that the blood-brain barrier may not be intact in AD.

Respiratory Disorders

TNFα has been shown to play a role in pulmonary fibrosis induced by bleomycin and silica (Piguet et al., Jour. Exper. Med., 170:655-663, 1989, and Nature, 344:245-247, 1990; Everson and Chandler, Amer. Jour. Path., 140:503-512, 1992; Phan and Kunkel, Exp. Lung Res. 18:29-43, 1992; also, Warren et al., Jour. Clin. Invest., 84:1873-1882, 1989; Denis et al., Amer. Jour. Cell Mol. Biol., 5:477-483, 1991). TNFα has been reported to orchestrate its proinflammatory effects by regulating the compartmentalized release of secondary messenger cytokines. Investigations have shown that nude mice exposed to chronic in vivo TNFα develop pulmonary inflammation and fibrosis (ARRD 145:A307, 1992).

Asthma

It has been reported that levels of TNFα are increased in bronchoalveolar lavage (BAL) fluid from patients with allergic asthma. Cirelli, et al. (1995) Amer. Jour. Resp. Critical Care Med., 151:345A; Redington et al., (1995) Amer. Jour. Respir. Crit. Care Med., 151: 702A. These findings indicate an increased tissue level of TNFα in asthma and that this may contribute to the pathophysiology of the condition.

Chronic Obstructive Pulmonary Disease (COPD)

Another disease state in which TNFα plays a role in the pathophysiology is chronic obstructive pulmonary disease. In silicosis, a disease of progressive respiratory failure caused by a fibrotic reaction, antibody to TNFα completely blocked the silica-induced lung fibrosis in mice (Piguet et al., Nature, 344:245-247, 1990). High levels of TNFα production (in the serum and in isolated macrophages) have been demonstrated in animal models of silica and asbestos induced fibrosis (Bissonnette et al., Inflammation, 13:329-339, 1989).

Adult Respiratory Distress Syndrome (ARDS)

Excessive TNFα concentrations, in excess of 12,000 pg/ml, have been detected in pulmonary aspirates from ARDS patients (Millar et al., Lancet, 2(8665):712-714, 1989). Systemic infusion of recombinant TNFα was shown to result in changes typically seen in ARDS (Ferrai-Baliviera et al., Arch. Surg., 124:1400-1405, 1989).

Lung Sarcoidosis

Alveolar macrophages from pulmonary sarcoidosis patients have been found to spontaneously release massive quantities of TNFα as compared with macrophages from normal donors (Baughman et al., Jour. Lab. Clin. Med., 115: 36-42, 1990). TNF-α also implicated in other acute disease states such as the pathophysiologic responses which follows subsequent reperfusion. It is involved in reperfusion injury, and is a major cause of tissue damage after loss of blood flow. (Vedder et al., Proc. Nat. Acad. Sci., 87:2643-2646, 1990).

Sepsis

Overproduction of TNF-α has been implicated in the pathogenesis of endotoxin induced septic shock, (see Carswell et al., Proc. Nat. Acad. Sci., 2:3666-3670, 1975). Endotoxin is the lipopolysaccharide component of the cell wall of gram-negative bacteria, and is a macrophage activator which induces the synthesis and enhanced secretion of TNF-α and other biologically active cytokine molecules. TNF-α is recognized as a central mediator of sepsis, septic shock and multiple organ failure. These host reactions are associated with increased blood levels of TNF-α, due to increased TNF-α production. (F. Stuber et al., Jour. Inflam., 46:42-50, 1996).

Liver Disorders

Because of its central role in metabolism and host defense mechanisms, the liver is thought to be major organ responsible for initiation of the multiple organ failure during sepsis. The depression in hepatocellular function in early, hyperdynamic stages of sepsis does not appear to be due to any reduction in hepatic perfusion, but is associated with elevated levels of circulating cytokines such as TNF-α. Furthermore, administration of recombinant TNF-α at doses that do not reduce cardiac output or hepatic perfusion, produces hepatocellular dysfunction. (P. Wang et al., Amer. Jour. Physiol., 270:5, 1996).

The role of TNF-α in induction of hepatic apoptosis under transcriptional arrest, activation of the 55 kDa receptor in the induction of hepatic apoptosis, the glycosylation step in TNF-induced hepatic apoptosis, hepatic injury induction by T cell-initiated cytokine release, and Ta cell-dependent TNF-mediated liver injury without transcriptional arrest has been reported. (A. Wendel et al., Cell. Biol. Mol. Basis Liver Transp., Int., Ringberg Conf. Hepatic Transp., 2nd, 1995, Pages 105-111).

Diabetes

TNF-α plays a central role in the state of insulin resistance associated with obesity. It has been previously shown that one important mechanism by which TNF-α interferes with insulin signaling is through serine phosphorylation of insulin receptor substrate-1 (IRS-1), which can function as an inhibitor of the tyrosine kinase activity of the insulin receptor (IR). The data strongly suggest that TNF-α inhibits signaling via a stimulation of p55 TNFR, and sphingomyelinase activity, which results in the production of an inhibitory form of IRS-1 (Peraldi et al., J. Biol. Chem. 271:13018-13022, 1996).

Crohn's Disease

TNF-α levels are elevated in Crohn's disease. In one study, TNF-α concentration was measured in stool samples from normal children, infants with diarrhea, and children with inflammatory bowel disease in active and inactive phases. Compared with diarrhea controls, stool TNF-α concentrations were significantly increased in children with active Crohn's disease. In patients with inactive Crohn's disease, either as a result of surgery, or treatment with steroids, the concentration of stool TNF-α fell to the level of the controls (C. P. Braegger et al., Lancet, 339:89-91, 1992).

Pre-Eclampsia

Pre-eclampsia is an endothelial disorder, and TNF-α has fundamental effects on endothelial cells by several means, including alteration of the balance between oxidant and antioxidant, changing the pattern of prostaglandin production, and affecting the expression of several cell surface components. In patients, results show that TNF-α mRNA expression is significantly elevated in preeclamptic patients compared to the control groups. These observations are consistent with a major role for TNF-α in the development of eclampsia (G. Chen et al., Clin. Exp. Immunol. 104:154-159, 1996).

Dermal Burns

The protein catabolic rate and TNF-α content of the soleus muscle of the scalded region and remote region were dynamically determined in the first week after the rats were inflicted with 37% TBSA full thickness scalding. The TNF-α content of skeletal muscles was far greater in the scalded region than in the remote region. TNF-.alpha. increase was also significantly correlated to the protein catabolic rate of the skeletal muscles (Li et al., Jour. Med. Coll., PLA 10:262-267, 1995; C.A. 125:938, 1245:8156a, 1996).

Bone Resorption

TNF-α is increased in bone resorption diseases, including arthritis, wherein it has been determined that when activated, leukocytes will produce a bone reabsorbing activity. Data indicate that TNF-α enhances this activity (Bertolini et al., Nature, 319:516-518, 1986, and Johnson et al., Endocrinology, 124:1424-1427, 1989). TNF-α stimulates bone resorption and inhibits bone formation in vitro and in vivo through stimulation of osteoclast formation and activation combined with inhibition of osteoblast function. TNF-α may be involved in many bone resorption diseases, including arthritis.

Rheumatoid Arthritis

Analysis of cytokine mRNA and protein in human rheumatoid arthritis tissue revealed that many proinflammatory cytokines such as TNF-α are abundant in all patients regardless of therapy. In rheumatoid joint cell cultures that spontaneously produce IL1, TNF-α was the major dominant regulator of IL1. Subsequently, other proinflammatory cytokines were also inhibited if TNF-α was neutralized, leading to the concept that the proinflammatory cytokines were linked in a network with TNF-α at its apex. This led to the concept that TNF-α was of major importance in rheumatoid arthritis. This has been successfully tested in animal models of collagen-induced arthritis, and these studies have provided the rationale for clinical trials of anti-TNF-α therapy in patients with long-standing rheumatoid arthritis. Several clinical trials using a chimeric anti-TNF-α antibody have shown marked clinical benefit, verifying the concept that TNF-α is of major importance in rheumatoid arthritis. Re-treatment clinical studies have also shown benefit in repeated relapses, indicating that the disease remains TNF-α dependent (M. Feldmann, Annual Rev. Immunol., 14:397-440, 1996).

Vascular Disorders

TNF-α alters the properties of endothelial cells and has various pro-coagulant activities, such as production of an increase in tissue factor procoagulant activity and suppression of the anticoagulant protein C pathway as well as down-regulating the expression of thrombomodulin (Sherry et al., Jour. Cell. Biol., 107:1269-1277, 1988). TNF-α has activities which, together with its early production (during the initial stages of a trauma or injury event), make it a mediator of response to tissue injury in several important disorders including, but not limited to myocardial infarction, stroke and circulatory shock. Of specific importance may be TNF-α induced expression of adhesion molecules, such as intercellular adhesion molecule (ICAM) or endothelial leukocyte adhesion molecule on endothelial cells (Munro et al., Am. Jour. Path., 135:121-132, 1989).

Cardiac Disorders

Evidence indicates that the current top suspects in heart failure are noradrenaline, angiotensin, vasopressin, endothelin, and tumor-necrosis factor (TNF-α) (N.E. J. Med., 323: 236-241, 1990). It has been reported that concentrations of TNF-α, which cause cachexia in chronic inflammatory disorders, infections, cancer and other diseases, are elevated in patients with severe heart failure, especially those with the more severe manifestations of the disease, such as cardiac cachexia.

Graft vs. Host Disease

In graft versus host reactions, increased serum TNF-α levels have been associated with major complications following acute allogenic bone marrow transplants (Holler et al., Blood, 75:1011-1016, 1990).

An subject antibody modulates, i.e., reduces or increases a symptom of the animal model disease or condition by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the antibody. In general, a subject antibody will cause a subject animal to be more similar to an equivalent animal that is not suffering from the disease or condition. Monoclonal antibodies that have therapeutic value that have been identified using the methods and compositions of the invention are termed "therapeutic" antibodies.

Kits

Also provided by the subject invention are kits for practicing the subject methods, as described above. The subject kits at least include one or more of: a subject antibody, a nucleic acid encoding the same, or a cell containing the same. The subject antibody may be humanized. Other optional components of the kit include: buffers, etc., for administering the antibody or for performing a TNFα activity assay. The nucleic acids of the kit may also have restrictions sites, multiple cloning sites, primer sites, etc. to facilitate their ligation to antibody nucleic acids. The various components of the kit may be present in separate containers or certain compatible components may be precombined into a single container, as desired.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Also provided by the subject invention are kits including at least a computer readable medium including programming as discussed above and instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means for producing antibodies that are less immunogenic in a host than a parent antibody, or nucleotide sequences them.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

EXAMPLES

Male human TNFα transgenic mice (with rheumatoid arthritis, RA), 7-8 weeks old, were purchased from Taconic and male normal mice, 6-7 weeks olds were obtained from the Animal Center, China Medical University. The transgenic mice were divided into three groups, and the mice of each of the three groups were either untreated (5 mice), treated with Humira from Abbot Laboratories (7 mice), or HZD RabMAb (7 mice). The HZD-M RAbMAb was produced by transient expression of cDNAs encoding SEQ ID NOS: 9 and 10 (FIG. 4) in HEK 293-6E cell and purified through a protein A column.

The mice were intraperitoneally injected with Humira (1 mg/kg), HZD-M RabMAb (1 mg/kg) or PBS (Non treatment and Normal group) 3 times a week (Monday, Wednesday and Friday) for 6 weeks. Body weight and arthritis scores were recorded weekly from one week before treatment to one week after the treatment completed. Arthritis was evaluated in ankle joints in a blind manner using a semiquantitative arthritis score as described previously.

Figure 2B:
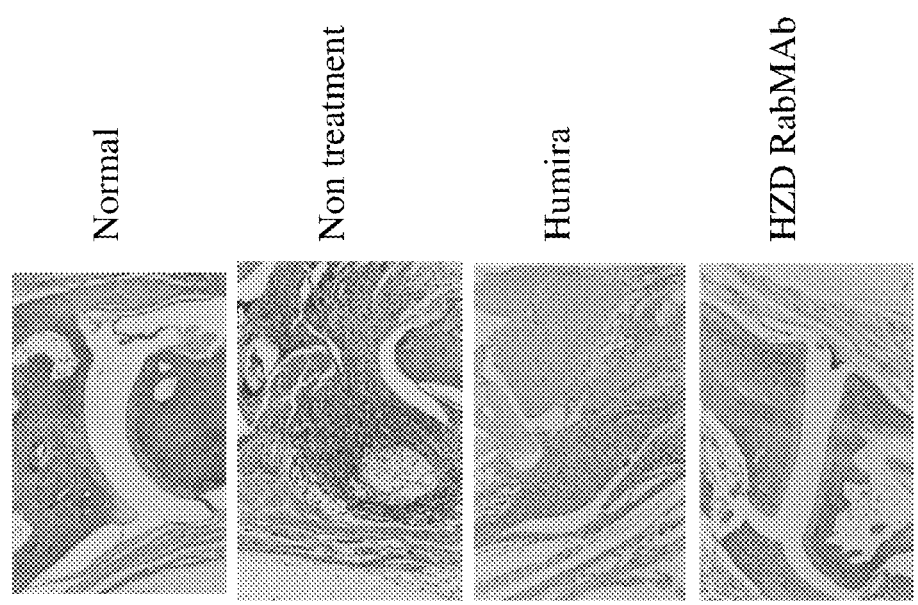
FIG. 2B shows representative sections through the ankles of those animals. Human TNFα transgenic mice with rheumatoid arthritis (RA) were treated with Humira or HZD RabMAb, and the RA score was compared to the non treatment group (A). Normal mice were used as a control. At the end of the treatment, histopathological studies on ankle joints were performed (B). Treatment with HZD RabMAb decreased RA scores toward to that for the normal mice and the ankle joints were also found as healthy as the normal mice.
Figure 3:
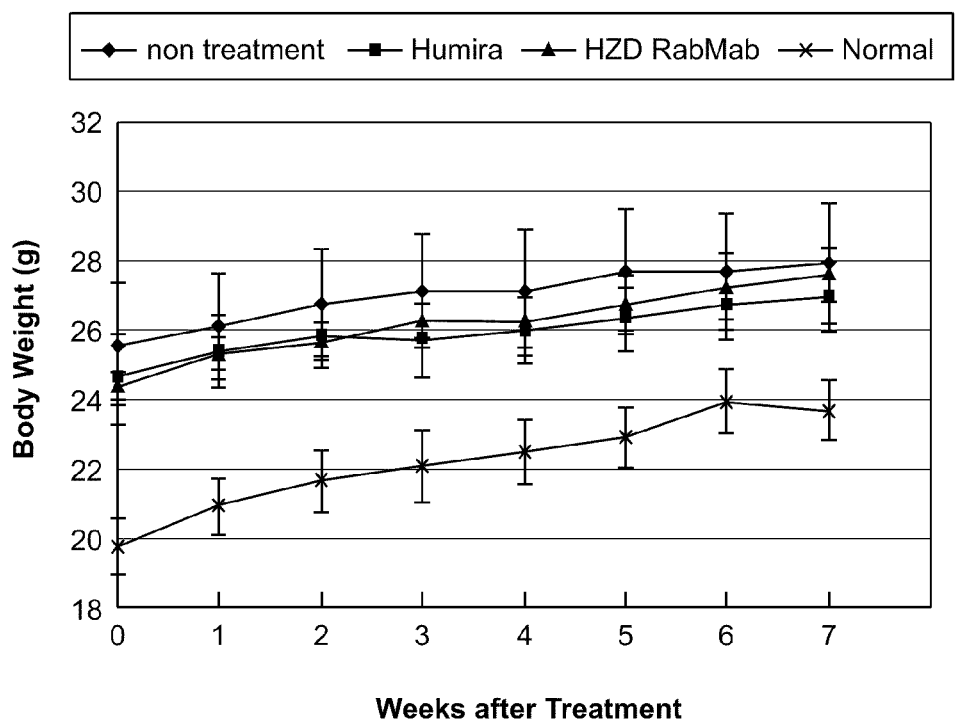
FIG. 3 is a graph showing the body weight for mice subjected to different treatments. No significant difference in body weight was observed between the non treatment and treated groups (Humira and HZD RabMAb) at the same time points in spite of some gain with time (C).

Results are shown in FIGS. 2A, 2B and 3. The score ranges from 0-3: 0=no arthritis (normal appearance and grip strength); 1=mild arthritis (joint swelling); 2 moderated arthritis (severe joint swelling and digit deformation, no grip strength); and 3 severe arthritis (ankylosis detected on flexion and severely impaired movement).

All mice were sacrificed one week after the treatment completed and ankle joints were removed for histology. The ankle joints were fixed in 10% buffered formalin overnight, decalcified in 30% formic acid for 4 days, and embedded in paraffin. Sections were stained with hematoxylin and eosin, and the histopathologic score was evaluated microscopically in a blinded manner using a scoring system as follows (Douni et al Attenuation of inflammatory polyarthritis in TNF transenic mice by Diacerein comparative analysis with dexamethasone methotrexate and anti-TNF protocol 2004 *Arthritis Res Ther* 6 (1) R65-R72; Wooley P. H. (1988) Collagen-induced arthritis in the mouse. Methods Enzymol. 162 361-373): 0=no detectable pathology; 1 hyperplasia of the synovial membrane and presence of polymorphonuclear infiltrates; 2 pannus and fibrous tissue formation and focal subchondral bone erosion; 3=articular cartilage destruction and bone erosin; and 4=extensive caticular cartilage destruction and bone erosion; and 4=extensive articular cartilage destruction and bone erosion.

An additional TNF-α-neutralizing antibody, HZD-M-Nterm, was constructed. This antibody was produced using human leader sequences and contained the variable domains of SEQ ID NOS:1 and 2 except for changes to amino acids at the N-terminus. The heavy chain variable domain of the HZD-M-Nterm antibody contains the amino acid sequence "QVQ" at the N-terminus rather than "QQ" as found in HZD-M. The light chain variable domain of the HZD-M-Nterm antibody contains the amino acid sequence "DIQ" at the N-terminus than "AYQ" as found in HZD-M. In certain cases, an antibody may have variable domains that are identical to those of HZD-M-Nterm.

It is evident from the above discussion that the subject invention provides an important new TNF-α-neutralizing antibody. Accordingly, the present invention represents a significant contribution to the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An antibody, comprising:
   a) a heavy chain variable domain comprising an amino acid sequence that is at least 95% identical to the amino acid sequence of SEQ ID NO. 1; and
   b) a light chain variable domain comprising an amino acid sequence that is at least 95% identical to the amino acid sequence of SEQ ID No. 2,
   wherein the antibody binds TNFα.

2. The antibody of claim 1, wherein said antibody is a monovalent antibody.

3. The antibody of claim 1, wherein said antibody is a bivalent antibody.

4. The antibody of claim 1, wherein said antibody is a single chain antibody.

5. The antibody of claim 1, wherein said antibody is a monoclonal antibody.

6. The antibody of claim 1, wherein said antibody comprises a single antigen binding arm and an Fc region.

7. The antibody of claim 1, wherein said antibody is humanized.

8. The antibody of claim 1, wherein the antibody is conjugated to an agent.

9. The antibody of claim 1, wherein said heavy chain variable domain comprises CDR regions that are identical to those shown in FIG. 1 and said light chain variable domain comprises CDR regions that are identical to those shown in FIG. 1 and wherein any changes in the amino acid sequence of said antibody relative to SEQ ID NOs: 1 and 2 occur in framework sequence.

10. The antibody of claim 1, where said antibody comprises CDRs that are otherwise identical to the CDRs of the antibody shown in FIG. 1 except for up to four amino acid substitutions in said CDRs.

11. A pharmaceutical composition comprising the antibody of claim 1 and a pharmaceutically acceptable carrier.

12. The antibody of claim 1, wherein said antibody comprises a) a heavy chain variable domain comprising an amino acid sequence that is identical to the amino acid sequence of SEQ ID NO. 1; and b) a light chain variable domain comprising an amino acid sequence that is identical to the amino acid sequence of SEQ ID No. 2, wherein the antibody binds TNFα.

* * * * *